United States Patent [19]

Marhold et al.

[11] Patent Number: 5,440,051
[45] Date of Patent: Aug. 8, 1995

[54] PROCESS FOR THE α-CHLORINATION OF ARYL ETHERS

[75] Inventors: Albrecht Marhold, Leverkusen; Klaus Jelich, Wuppertal, both of Germany

[73] Assignee: Bayer Aktiengesellschaft, Leverkusen, Germany

[21] Appl. No.: 216,239

[22] Filed: Mar. 22, 1994

Related U.S. Application Data

[63] Continuation of Ser. No. 48,165, Apr. 15, 1993, abandoned.

[30] Foreign Application Priority Data

Apr. 27, 1992 [DE] Germany .................... 42 13 849.3

[51] Int. Cl.⁶ .............................. C07D 319/14
[52] U.S. Cl. ...................... 549/362; 549/365; 549/437; 568/649; 568/655; 568/656
[58] Field of Search ............. 549/362, 365, 367; 568/649, 655, 656

[56] References Cited

U.S. PATENT DOCUMENTS 3,784,611  1/1974  Larsen et al. ..................... 568/649

FOREIGN PATENT DOCUMENTS

| 0347677 | 12/1989 | European Pat. Off. ........... 568/649 |
| 3821130 | 12/1989 | Germany . |
| 675122 | 8/1990 | Switzerland ...................... 568/649 |
| 676119 | 12/1990 | Switzerland ...................... 568/649 |
| 712478 | 11/1951 | United Kingdom ................ 568/655 |

OTHER PUBLICATIONS

*Societe Francaise de Chimie*, 11–12/86, cover page & pp. 925–929, Bulletin de la Societe Chimique de Frances; "A Safe and Economical Synthesis of 3-(trifluoromethoxy)aniline from 2-chlorophenol", B. Langlois et al, (Jun. 1986).
Houben-Weyl, Bd. E4, pp. 633–634 (Dec. 1983).

*Primary Examiner*—James H. Reamer
*Attorney, Agent, or Firm*—Sprung Horn Kramer & Woods

[57] ABSTRACT

Aryl ethers are chlorinated in the α-position by a process in which they are metered into a reaction vessel at the same time as chlorine, the reaction being carried out at temperatures in the range from 60° to 150° C.

14 Claims, No Drawings

PROCESS FOR THE α-CHLORINATION OF ARYL ETHERS

This application is a continuation of application Ser. No. 08/048165 filed Apr. 15, 1993 now abandoned.

It is already known that trichloromethoxybenzene can be prepared by placing methoxybenzene in carbon tetrachloride, heating the solution to the boil under reflux and then introducing chlorine (see Houben-Weyl, Methoden der organischen Chemie (Methods of Organic Chemistry), volume E4, page 633 (1983)). It is also possible to prepare aryloxychloromethanes from aryloxymethanes by radical-initiated chlorination, wherein either chlorine is introduced into aryloxymethane, or a mixture of aryloxymethane and sulphuryl chloride is heated (see German Offenlegungsschrift 3 821 130). The disadvantages of these processes are that the reactions are carried out in dilute solutions, resulting in unfavourable space-time yields, and that carbon tetrachloride, which is an environmental pollutant, is used as solvent.

A process has now been found for the α-chlorination of aryl ethers of formula (I):

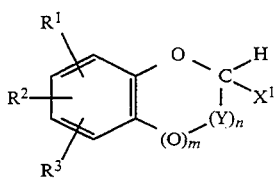

in which

R$^1$, R$^2$ and R$^3$ independently of one another are in each case hydrogen, fluorine, chlorine, CF$_3$, OCF$_3$, OCHF$_2$, OCF$_2$CF$_2$H or OCF$_2$Cl, X$^1$ is hydrogen, fluorine, chlorine or CF$_3$, m is zero or 1 and in the case where m=zero, n is 1 and Y is hydrogen, chlorine or fluorine, and in the case where m=1, n is zero or 1 and Y is CH$_2$, CHCl, CCl$_2$ or CF$_2$, which process is characterised in that aryl ethers of formula (I) are metered into a reaction vessel at the same time as chlorine, the reaction being carried out at temperatures in the range from 60 to 150° C.

The aryl ethers which are preferably used in the process according to the invention are those of formula (I) in which R$^1$ and R$^2$ independently of one another are hydrogen, fluorine, chlorine, CF$_3$ or OCF$_3$, R$^3$ is hydrogen, X$^1$ is hydrogen, fluorine, chlorine or CF$_3$, m is zero or 1 and in the case where m=zero, n is 1 and Y is hydrogen, and in the case where m=1, n is zero or 1 and Y is CH$_2$ or CF$_2$.

Aryl ethers which are particularly preferably used are those of formula (I) in which R$^1$ is hydrogen, fluorine or chlorine, R$^2$ and R$^3$ are hydrogen, X$^1$ is hydrogen or CF$_3$, m is zero or 1 and in the case where m=zero, n is 1 and Y is hydrogen, and in the case where m=1, n is zero.

An essential feature of the present invention is that aryl ethers of formula (I) are metered into a reaction vessel at the same time as chlorine. A possible procedure is for example to meter all the aryl ether of formula (I) to be used, or the bulk of it, into a reaction vessel at the same time as chlorine. If it is desired to meter the bulk of the aryl ether into a reaction vessel at the same time as chlorine, it is possible first to introduce e.g. 0.5 to 49% by weight of the total amount of aryl ether to be used, and to meter in 99.5 to 51% by weight of the total amount of aryl ether to be used at the same time as the chlorine. In such cases, it is preferable first to introduce 5 to 45% by weight of the total amount of aryl ether to be used, and to meter in 95 to 55% by weight of the total amount of aryl ether to be used with the chlorine. In these cases, it is particularly preferable first to introduce 8 to 40% by weight of the total amount of aryl ether to be used, and to meter in 92 to 60% by weight of the total amount of aryl ether to be used at the same time as the chlorine.

The process according to the invention is preferably carried out at 65 to 135° C., especially at 70 to 120° C.

The process according to the invention can be carried out in the absence or presence of a solvent.

Suitable solvents for the process according to the invention are those from the group consisting of chlorination products of aryl ethers of formula (I), fluorination products of chlorination products of aryl ethers of formula (I), and inert aromatic solvents.

Chlorination products of the aryl ethers of formula (I) have e.g. formula (II):

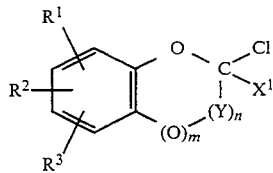

In formula (II), RR$^1$, R$^2$, R$^3$, X$^1$, m, n and Y are as defined for formula (I). X$^1$ here is preferably chlorine and Y here is preferably chlorine or fluorine in the case where m=zero and preferably CCl$_2$ or CF$_2$ in the case where m=1.

Chlorination products of aryl ethers of formula (I) which are suitable as solvents for the process according to the invention are preferably trichloromethoxybenzene and trichloromethoxybenzenes having the following substituents: 2-chloro, 3-chloro, 4-chloro, 2,3-dichloro, 2,4-dichloro, 2,5-dichloro, 2,6-dichloro, 2-fluoro, 3-fluoro, 4-fluoro, 2,4-difluoro, 2-trifluoromethyl, 3-trifluoromethyl, 4-trifluoromethyl, 2-trifluormethyl-3-chloro, 2-trifluoromethyl-4-chloro, 2-trifluoromethyl-5-chloro, 4-trifluoromethyl-3-chloro and 2,3,4-trifluoromethoxy, as well as 2,2-dichlorobenzodioxole and 2,2-dichlorobenzodioxoles having the following substituents: 4-chloro, 5-chloro, 4-fluoro and 5-fluoro.

Chlorination products of aryl ethers of formula (I) can also be mixtures of different compounds and/or crude and/or isolated chlorination products from a previous batch.

Chlorination products of aryl ethers of formula (I) are often processed further, the chlorine atoms in the α-position being completely or partially exchanged with fluorine atoms using fluorinating agents. Thus, for example, trifluoromethoxybenzene, chlorodifluoromethoxybenzene and/or dichlorofluoromethoxybenzene are obtained from trichloromethoxybenzene. Such fluorination products of chlorination products of aryl ethers of formula (I) can also be used as solvents for the process according to the invention, e.g. as pure products, in a mixture with one another, in a mixture with chlorination products of aryl ethers of formula (I), and/or as crude and/or isolated products of the fluorination of chlorination products of aryl ethers of formula (I).

Examples of suitable inert aromatic solvents are chlorobenzene, dichlorobenzenes, benzotrifluoride, chlorobenzotrifluorides, bistrifluoromethylbenzenes, bistrifluoromethoxybenzenes, chloro-bistrifluoromethylbenzenes and fluorochlorobenzenes. Inert aromatic solvents can be used as such, in a mixture with one another, and/or in a mixture with chlorination products of aryl ethers of formula (I), and/or in a mixture with fluorination products of chlorination products of aryl ethers of formula (I).

If solvents are used in the process according to the invention, the amounts can be for example from 5 to 100% by weight, based on the total amount of aryl ether of formula (I) used. This amount is preferably from 5 to 50% by weight, especially from 5 to 20% by weight.

The chlorination according to the invention is carried out with elemental chlorine, which is generally introduced into the reaction mixture in the form of the undiluted gas.

The process according to the invention can generally be carried out without the addition of chlorination catalysts, although these can be added if appropriate. Examples of chlorination catalysts are phosphorus trichloride, phosphorus oxychloride, phosphorus pentachloride, potassium chloride and mixtures thereof. Chlorination catalysts can be used e.g. in amounts from 0 to 15% by weight (based on the total amount of aryl ether of formula (I) used).

In one particular embodiment of the present invention, the reaction is carried out in the presence of a radical-forming agent or UV light. Examples of suitable radical-forming agents are benzoyl peroxide, diacetyl peroxide, succinyl peroxide or azobisisobutyronitrile. Radical-forming agents can be used e.g. in amounts from 0 to 10% by weight. (based on the total amount of aryl ether of formula (I) used).

It is also possible to use chlorination catalysts combined with radical-forming agents or UV light.

The end of the chlorination reaction, and hence the point at which the introduction of chlorine is ended, can be determined for example by gas chromatography.

The mixture present after the end of the chlorination reaction can for example first be purged with an inert gas, e.g. nitrogen, after which the solvent and, if appropriate, the reaction product can optionally be separated from higher-boiling by-products by distillation.

The products obtainable according to the invention can be reacted for example with fluorinating agents and the fluorinated compounds thereby obtainable can be used for the preparation of e.g. plant protection agents. Thus, for example, difluorobenzodioxole is an intermediate for fungicides described in European patent application A-333 658 and for the insecticide Alsystin ® (CAS no. 64 628-44-0).

The process according to the invention has a number of advantages. Thus, in contrast to the state of the art, the reaction can be carried out without a solvent or in more concentrated solutions, resulting in markedly higher space-time$_e$ yields. Furthermore, carbon tetrachloride, which is an environmental pollutant, is avoided as a solvent. Finally, the use of the chlorination products of the process according to the invention as solvents, or the use of fluorination products of the chlorination products, is particularly advantageous in terms of technology, process technology and economics, since these solvents are inherent in the system.

EXAMPLES

Example 1

30 g of 4-chloroanisole at 80° to 85° C. were placed in a chlorination apparatus equipped with an immersion lamp, 5 g of phosphorus trichloride were added and chlorine was introduced under irradiation with UV light. When the chlorine uptake died down, further 4-chloroanisole was metered in and the introduction of chlorine was continued. After a total of 200 g of 4-chloroanisole had been added, the end of the chlorination was verified by gas chromatography and the chlorine supply was then stopped. After purging with nitrogen, the batch was distilled to give 310 g of 4-chloro-trichloromethoxybenzene (boiling point: 122°–126° C./16 mbar, refractive index $n_D^{20}$: 1.5565), corresponding to a yield of 89.8% of theory.

Example 2

The dropping funnel on a glass apparatus was filled with 70 g of 4-chloroanisole in which 2 g of azobisisobutyronitrile were dissolved. After the reaction flask, already containing 50 g of 4-chloroanisole, had been heated to 80° C., the contents of the dropping funnel were slowly added dropwise and chlorine was introduced at the same time. The amount of chlorine was regulated so that the reaction temperature did not exceed 90° C. Over a period 9 hours, chlorine and starting material were metered in such a way that at the beginning more chlorine was introduced in order to chlorinate the initial amount, and towards the end the amount of chlorine corresponded approximately to the stoichiometrically required amount (relative to the amount of 4-chloroanisole metered in). The batch was then purged with nitrogen and distilled to give 7 g of first runnings, which could be reused in the chlorination, and 167 g of 4-chloro-trichloromethoxybenzene. The residue amounted to 21 g. The isolated amount of 4-chloro-trichloromethoxybenzene corresponded to 80.7% of theory.

Example 3

50 g of 4-chloro-trichloromethoxybenzene, 1 g of phosphorus trichloride and 1 g of potassium chloride were placed in a glass apparatus. The dropping funnel on the glass apparatus was charged with 120 g of 4-chloroanisole and 2 g of azobisisobutyronitrile. After the contents of the flask had been heated to 80° C., the contents of the dropping funnel were slowly added dropwise to the reaction vessel and the chlorine supply was started at the same time. The subsequent procedure was as in Example 2. 219 g of 4-chloroanisole were obtained.

Example 4

The procedure was as in Example 3 except that the 4-chloro-trichloromethoxybenzene was replaced with 50 g of 4-chloro-trifluoromethoxybenzene. After the distillation, 4-chloro-trifluoromethoxybenzene was recovered together with some 4-chloro-dichloromethoxybenzene and 4-chloro-trichloromethoxybenzene, which could be fed into the next batch. The yield of 4-chloro-trichloromethoxybenzene was 186 g.

Example 5

200 g of 2-chloroanisole and 5 g of azobisisobutyronitrile were placed in the dropping funnel of a glass chlorination apparatus equipped with a chlorine inlet, a reflux condenser, a gas outlet and a dropping funnel. 5 g of phosphorus trichloride were placed in the flask and heated to 80° C. 50 g of the contents of the dropping funnel were then run in, after which chlorine was metered in at 80 to 90° C. After about 60 g of chlorine had been metered in, more mixture from the dropping funnel was again metered in as well as the chlorine. The end point of the chlorination was reached after 8 hours (monitoring by gas chromatography). After the batch had been purged with dry nitrogen, it was distilled to give 310 g (=89.8% of theory) of 2-chloro- trichloromethoxybenzene (boiling point: 126–°130° C./16 mbar) and 40 g of an acetone-soluble residue.

Example 6

The procedure was as in Example 5 except that 50 g of 2chlorobenzotrifluoride were placed in the flask together with 5 g of phosphorus trichloride. The metering and chlorination were otherwise carried out analogously. The solvent was recovered by distillation and a distillate of 309 g of 2-chloro-trichloromethoxybenzene was obtained. The recovered solvent still contained a proportion of incompletely chlorinated material and could be reused.

Example 7

0.5 g of potassium chloride and 10 g of difluoromethoxybenzene were placed in 100 ml of 1,3-bistrifluoromethylbenzene and chlorine was then introduced at 100° C. under UV irradiation. A further 20 g of difluoromethoxybenzene were metered in over a period of 1 hour. When the chlorine uptake had ended, the mixture was purged with nitrogen and then distilled to give 35.5 g of chlorodifluoromethoxybenzene (boiling point: 144° C., refractive index $n_D^{20}$: 1.4479).

Example 8

The procedure was as in Example 7 except that the difluoromethoxybenzene was replaced with 100 g of 2,2,2-trifluoroethoxybenzene. 10 g of this were introduced at the beginning and the remaining 90 g were metered in together with the chlorine. 101.5 g of 1,1-dichloro-2,2,2trifluoroethoxybenzene were obtained (boiling point: 77°–80° C./20 mbar, refractive index $n_D^{20}$: 1.4615).

Example 9

600 g of chlorobenzene at 110° C. were placed in a stirred apparatus equipped with a chlorine inlet, a metering device, a high-efficiency condenser and a gas outlet, and a solution of 18 g of azobisisobutyronitrile in 900 g of benzodioxole was then metered in slowly (75 to 80 g per hour) and 100 to 105 g of chlorine per hour were introduced at the same time. The reaction was exothermic and was kept at 110° C. by removing the heating bath. When the metering of benzodioxole and chlorine was complete, chlorine was introduced for a further 30 minutes and the mixture was then purged with nitrogen and distilled. After the withdrawal of 630 g of a first fraction (chlorobenzene and reusable chlorination product), 1240 g of 2,2-dichlorobenzodioxole were obtained (boiling point: 81°–90° C./12 mbar).

Example 10

60 g of dichlorobenzodioxole at 130° C. were placed in a stirred apparatus equipped with a chlorine inlet, a metering device, a high-efficiency condenser and a gas outlet, and a solution of 1.8 g of azobisisobutyronitrile in 122 g of benzodioxole was then metered in over a period of 3 hours and 150 g of chlorine were introduced at the same time. When the metering had ended, the mixture was purged at 130° C. with nitrogen. 228 g of 2,2dichlorobenzodioxole with a boiling point of 81°–90° C at 12 mbar were obtained.

The crude product of the chlorination (250 g) could be used without further purification in a fluorination for the preparation of 2,2-difluorobenzodioxole.

Example 11

490 g of 3,5-bis-fluoromethyl-phenol were placed in 1000 ml of acetone together with 50 g of 50% by weight aqueous sodium hydroxide solution, and hexafluoropropene was introduced at 25° C. up to the saturation point. The batch was then diluted with 1l of water and the organic phase was separated off, dried and distilled to give 673 g of 3,5-bis-fluoromethyl-phenyl 1,1,2,3,3,3-hexafluoropropyl ether with a boiling point of 65° to 70° C. at 22 mbar and a refractive index $n_D^2$ of 1.3560.

The product obtained in this way was treated with chlorine for 3 hours at the reflux temperature under UV irradiation. No chlorination products were found on subsequent examination by gas chromatography.

3,5-Bis-fluoromethyl-phenyl 1,1,2,3,3,3-hexafluoropropyl ether is therefore suitable as a solvent for the process according to the invention for the e-chlorination of aryl ethers.

Example 12

200 g of 2,3-dichloro-benzo-1,4-dioxene were placed in 500 ml of 1,4-bis-fluoromethylbenzene and heated to 110° C. Chlorine was introduced under UV irradiation and the progress of the chlorination was monitored by means of gas chromatographic analysis. When the conversion was complete, the chlorine supply was stopped and the reaction vessel was purged with nitrogen. Distillation gave 240 g of 2,2,3,3-tetrachloro-benzo-1,4-dioxene with a boiling point of 140° to 142° C. at 20 mbar and a melting point of 88° to 92° C.

What is claimed is:

1. A process for the α-chlorination of aryl ethers of formula (I):

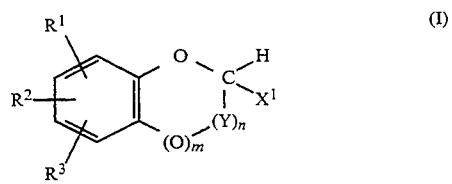

in which $R^1$, $R^2$ and $R^3$ independently of one another represent hydrogen,
fluorine, chlorine, $CF_3$, $OCF_3$, $OCHF_2$, $OCF_2CF_2H$, or $OCF_2Cl$,
$X^1$ is hydrogen, fluorine, chlorine or $CF_3$,
m is zero or 1 and
when
   m=zero, n is 1 and Y is hydrogen, chlorine or fluorine, and
when
   m=1, n is zero or 1 and Y is $CH_2$, CHCl, $CCl_2$ or $CF_2$,
in which process, in the presence of chlorination products of an aryl ether of formula (I), in the presence of fluorination products of chlorination products of aryl ether of formula (I), or in the presence of an inert aromatic solvent, all the aryl ether of formula (I) to be used is metered into a reaction vessel at the same time as chlorine, the reaction being carried out at temperature in the range from 60° to 150° C.

2. The process of claim 1, in which an aryl ether of formula (I) is used in which
   $R^1$ and $R^2$ independently of one another are hydrogen, fluorine, chlorine, $CF_3$ or $OCF_3$,
   $R^3$ is hydrogen
   $X^1$ is hydrogen, fluorine, chlorine or $CF_3$,
   m is zero or 1 and
in the case where
   m=zero, n is 1 and Y is hydrogen, and
in the case where
   m=1, n is zero or 1 and Y is $CH_2$ or $CF_2$.

3. The process of claim 1, which is carried out without the addition of chlorination catalysts.

4. The process of claim 1, which is carried out in the presence of 5 to 100% by weight of solvent, based on the total amount of the aryl ether of formula (I) used.

5. The process of claim 1, which is carried out in the presence of a chlorination catalyst selected from one or more members of the group consisting of phosphorus trichloride, phosphorus oxychloride, phosphorus pentachloride and potassium chloride.

6. The process of claim 1, which is carried out in the presence of a radical forming agent or UV light.

7. The process of claim 1, in which the point at which the introduction of chlorine is ended is determined by gas chromatography.

8. The process of claim 1, wherein said reaction is carried out at a temperature in the range 65° to 135° C.

9. A process for the α-chlorination of aryl ethers of formula (I)

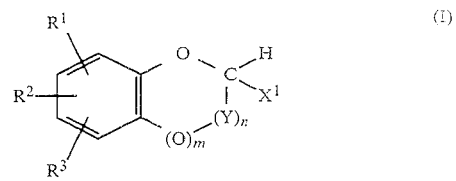

in which
   $R^1$, $R^2$ nd $R^3$ independently of one another represent hydrogen, fluorine, chlorine, $CF_3$, $OCF_3$, $OCHF_2$, $OCF_2CF_2H$, or $OCF_2Cl$,
   $X^1$ is hydrogen, fluorine, chlorine or $CF_3$,
   m is zero or 1 and
when
   m=zero, n is 1 and Y is hydrogen, chlorine or fluorine, and
when
   m=1, n is zero or 1 and Y is $CH_2$, CHCl, $CCl_2$ or $CF_2$,
in which process, in the absence of solvents, 0.5 to 49% by weight of the total amount of the aryl ether of formula (I) to be used is introduced first and 99.5 to 51% by weight of the total amount of the aryl ether to be used is metered into a reaction vessel at the same time as chlorine, the reaction being carried out at temperature in the range from 60° to 150° C.

10. The process of claim 9, in which an aryl ether of formula (I) is used in which
   $R^1$ and $R^2$ independently of one another are hydrogen, fluorine, chlorine, $CF_3$ or $OCF_3$,
   $R^3$ is hydrogen,
   $X^1$ is hydrogen, fluorine, chlorine or $CF_3$,
   m is zero or 1 and
in the case where
   m=zero, n is 1 and Y is hydrogen, and
in the case where
   m=1, n is zero or 1 and Y is $CH_2$ or $CF_2$.

11. The process of claim 9, which is carried out without the addition of chlorination catalysts.

12. The process of claim 9, which is carried out in the presence of a chlorination catalyst selected from one or more members of the group consisting of phosphorus trichloride, phosphorus oxychloride, phosphorus pentachloride and potassium chloride.

13. The process of claim 9, which is carried out in the presence of radical-forming agent or UV light.

14. The process of claim 9, in which the point at which the introduction of chlorine is ended is determined by gas chromatography.

* * * * *